United States Patent [19]
Miyata et al.

[11] Patent Number: 5,750,774
[45] Date of Patent: May 12, 1998

[54] METHOD FOR PRODUCING N-PHOSPHONOMETHYLGLYCINE

[75] Inventors: Hideo Miyata, Kanagawa; Toru Sasaki, Fukushima; Kohei Morikawa, Kanagawa, all of Japan

[73] Assignee: Showa Denko K.K., Tokyo, Japan

[21] Appl. No.: 814,827

[22] Filed: Mar. 11, 1997

Related U.S. Application Data

[60] Provisional application No. 60/013,146, Mar. 11, 1996.

[51] Int. Cl.$^6$ .................................................. C07F 9/38
[52] U.S. Cl. .................................................. 562/17
[58] Field of Search .................................................. 562/17

[56] References Cited

U.S. PATENT DOCUMENTS

| | | | |
|---|---|---|---|
| 3,923,877 | 12/1975 | Barton | 260/502.5 |
| 4,221,583 | 9/1980 | Gaertner et al. | 71/86 |
| 5,324,855 | 6/1994 | Morikawa et al. | 562/16 |
| 5,453,537 | 9/1995 | Morikawa et al. | 562/17 |
| 5,679,844 | 10/1997 | Miyata | 562/17 |

FOREIGN PATENT DOCUMENTS

| | | | |
|---|---|---|---|
| 0 717 046 A1 | 6/1996 | European Pat. Off. | C07F 9/38 |

OTHER PUBLICATIONS

Chemical Abstracts, vol. 118, No. 5, 1 Feb. 1993, Abstract No. 039415.
Chemical Abstracts, vol. 124, No. 23, 3 Jun. 1996, Abstract No. 317885.
Chemical Abstracts, vol. 125, No. 17, 1996, Abstract No. 222444.

*Primary Examiner*—Samuel Barts
*Attorney, Agent, or Firm*—Sughrue, Mion, Zinn, Macpeak & Seas, PLLC

[57] ABSTRACT

The present invention provides a method for producing N-phosphonomethylglycine which comprises reacting an aminomethylphosphonic acid with glycolonitrile, or formaldehyde and hydrogen cyanide in situ, under an alkaline condition to convert the aminomethylphosphonic acid into an N-phosphonomethylglycinonitrile salt or a mixture of an N-phosphonomethylglycinonitrile salt and N-phosphonomethylglycinonitrile, and then hydrolyzing the product under an acidic condition. Subsequent to a reaction step for the production of N-phosphonomethylglycinonitrile, the reaction product is hydrolyzed by adding thereto an acid in a prescribed amount. Accordingly, the use of a large amount of an alkaline metal hydroxide and the neutralization step for obtaining N-phosphonomethylglycine after hydrolysis, which steps are necessary in a conventional alkali hydrolysis method, are omitted in the present invention.

10 Claims, No Drawings

METHOD FOR PRODUCING N-PHOSPHONOMETHYLGLYCINE

CROSS REFERENCE TO RELATED APPLICATION

This application is an application filed under 35 U.S.C. §111(a) claiming benefit pursuant to 35 U.S.C. §119(e)(i) of the filing date of the Provisional Application 60/013,146, filed Mar. 11, 1996, pursuant to 35 U.S.C. §111(b).

FIELD OF THE INVENTION

The present invention relates to a method for producing N-phosphonomethylglycine which is useful as a herbicide.

BACKGROUND OF THE INVENTION

The agricultural chemical N-phosphonomethylglycine and salts thereof are biodegradable and are effective as herbicides when used in a small quantities. Accordingly, the subject chemical is widely used in agriculture.

A large number of methods for producing N-phosphonomethylglycine are known.

Examples of the method for producing N-phosphonomethylglycine using an aminomethylphosphonic acid as a starting material include adding an aminomethylphosphonic acid in an aqueous glyoxal solution at a temperature of from 40° to 45° C., and then heating the mixed solution (Japanese Unexamined Patent Publication No. 62-61992); reacting an aminomethylphosphonic acid and glyoxal as raw materials in the presence of sulfur dioxide (European Patent 81459 and U.S. Pat. No. 4,369,142); reacting an aminomethylphosphonic acid with glyoxalic acid, and then reducing the reaction product with hydrogen in the presence of a palladium catalyst (European Patent 186648); heating an aminomethylphosphonic acid and chloroacetic acid at a temperature of approximately from 80° to 120° C. in the presence of an acid acceptor such as sodium hydroxide (Polish Patent 120759 and Spanish Patent 504479); and reacting an aminomethylphosphonic acid with diethyl bromomalonate under an alkaline condition, and then hydrolyzing the reaction product with sulfuric acid (Spanish Patent 545456).

The above-described methods employ a gas that is difficult to handle, involve a cumbersome reaction operation, or suffer from insufficient reaction yields. Thus, these methods are not entirely satisfactory for industrial production.

U.S. Pat. No. 4,221,583 discloses a method for producing N-phosphonomethylglycinonitrile or a mono salt thereof comprising reacting an aminomethylphosphonic acid with formaldehyde in the presence of an alkali (where the alkali is necessary for forming a mono salt of the aminomethylphosphonic acid), to thereby convert the aminomethylphosphonic acid into an N-methylol form, and reacting potassium cyanide therewith at a pH of from 7 to 10. This patent publication discloses that N-phosphonomethylglycine is obtained by hydrolyzing the N-phosphonomethylglycinonitrile synthesized by the above-described method. However, in the Example of this patent publication, the yield of N-phosphonomethylglycinonitrile at best is 66%. In order to increase the conversion ratio of the aminomethylphosphonic acid, a large excess of potassium cyanide in an amount of 2.4 equivalents to the aminomethylphosphonic acid is required. Furthermore, the yield in hydrolysis of N-phosphonomethylglycinonitrile according to the Example thereof is at best 90%. Accordingly, the yield of N-phosphonomethylglycine based on the aminomethylphosphonic acid starting material is about 60%.

In view of the above, the present inventors previously proposed a method for producing N-phosphonomethylglycine using an aminomethylphosphonic acid as a raw material, which method is easy to practice and provides excellent yield. This method comprises reacting an aminomethylphosphonic acid with glycolonitrile in the presence of an alkali metal hydroxide, and then adding thereto an alkali metal hydroxide in an amount sufficient to neutralize the carboxylic acid that is produced to thereby effect hydrolysis (Japanese Unexamined Patent Publication No. 4-279585).

According to this method, the conversion ratio of each of the aminomethylphosphonic acid and the glycolonitrile is 95% or more, and the selectivity of N-phosphonomethylglycine is 95% or more.

This method follows a conventional technique. Namely, when the nitrile group of a nitrile derivative having an acidic hydroxyl group derived from a phosphoric acid, such as N-phosphonomethylglycinonitrile, is hydrolyzed into a carboxylic acid, the reaction is conducted by protecting the acidic hydroxyl group as a stable alkali metal salt. The alkali hydrolysis used in this method requires a neutralization step comprising adding an acid after the hydrolysis to thereby obtain free N-phosphonomethylglycine.

U.S. Pat. No. 4,221,583 cited above discloses that free N-phosphonomethylglycinonitrile can be converted into N-phosphonomethylglycine by hydrolyzing with an acid or an alkali. In the Example thereof, N-phosphonomethylglycine is obtained by boiling N-phosphonomethylglycinonitrile (0.9 g) with an excess amount (50 ml) of hydrochloric acid and water (100 ml).

An object of the present invention is to provide a method for producing N-phosphonomethylglycine which dispenses with the need for a neutralization step that is otherwise required when reacting an aminomethylphosphonic acid with glycolonitrile under alkaline conditions and hydrolyzing the reaction product under alkaline conditions.

As a result of extensive investigations on a method for producing N-phosphonomethylglycine comprising reacting an aminomethylphosphonic acid with glycolonitrile under an alkaline condition and then hydrolyzing the reaction product, the present inventors found that N-phosphonomethylglycine can be obtained in high yield when N-phosphonomethylglycinonitrile or a salt thereof (obtained by reacting an aminomethylphosphonic acid with glycolonitrile under an alkaline condition) is hydrolyzed under an acidic condition by adding thereto an appropriate amount of an acid. The present invention, is based on this finding.

According to the method of the present invention, an acidic solution of N-phosphonomethylglycine is concentrated and the pH is adjusted, as needed, to crystallize and isolate N-phosphonomethylglycine. As a result, an alkali neutralization step is omitted that is otherwise required in a method which relies on alkali hydrolysis.

SUMMARY OF THE INVENTION

The present invention provides:

(1) A method for producing N-phosphonomethylglycine which comprises reacting an aminomethylphosphonic acid with glycolonitrile, or formaldehyde and hydrogen cyanide in situ, under an alkaline condition to obtain a product comprising an N-phosphonomethylglycinonitrile salt or a mixture of an N-phosphonomethylglycinonitrile salt and N-phosphonomethylglycinonitrile, and adding an acid to hydrolyze the product under an acidic condition;

2) A method for producing N-phosphonomethylglycine as described in (1) above, which comprises adding the acid for hydrolysis in an amount needed to neutralize the reaction solution obtained by reacting an aminomethylphosphonic acid with glycolonitrile under an alkaline condition, and further adding the acid in an amount of 0.5 equivalents or more to the N-phosphonomethylglycinonitrile; and 3) A method for producing N-phosphonomethylglycine as described in (1) or (2) above, which comprises reacting an aminomethylphosphonic acid and glycolonitrile in an amount of from 0.5 to 1.5 equivalents to the aminomethylphosphonic acid in the presence of an alkali metal hydroxide or an alkaline earth metal hydroxide, wherein the alkali metal hydroxide or the alkaline earth metal hydroxide is added in an amount of from 1.5 to 2.5 equivalents to the aminomethylphosphonic acid.

Other preferred embodiments of the present invention are as follows:

(4) A method for producing N-phosphonomethylglycine as described in (1) or (2) above, which comprises adding hydrochloric acid or sulfuric acid to hydrolyze the product; and (5) A method for producing N-phosphonomethylglycine as described in (3) above, wherein the alkali metal hydroxide comprises sodium hydroxide or potassium hydroxide.

DETAILED DESCRIPTION OF THE INVENTION

The present invention is described in greater detail below.

1. N-phosphonomethylglycinonitrile:

N-phosphonomethylglycinonitrile or a salt thereof for use as a raw material in the hydrolysis reaction of the present invention can be produced by a conventional method. A preferred example is a method where the reaction of an aminomethylphosphonic acid with glycolonitrile is conducted by adding an alkali metal hydroxide or an alkaline earth metal hydroxide (hereinafter referred to as an alkaline metal hydroxide) as described in Japanese Unexamined Patent Publication No. 3-64026. In this method, an alkaline metal hydroxide is used because the aminomethylphosphonic acid is an amphoteric compound having an amino group and a phosphono group within the same molecule, and the amino group of the aminomethylphosphonic acid must not be in the form of an ion for reacting the aminomethylphosphonic acid with glycolonitrile. When at least one of two acidic hydroxyl groups of the aminomethylphosphonic acid is not neutralized with the alkaline metal hydroxide, as found in general amphoteric compounds, a part or almost all of the amino groups of the aminomethylphosphonic acid are in the form of ions, namely, amphoteric ions, and the aminomethylphosphonic acid does not react with glycolonitrile.

Accordingly, the alkaline metal hydroxide is preferably added in an amount of 2 equivalents to the aminomethylphosphonic acid. The molar ratio of the alkaline metal hydroxide to the aminomethylphosphonic acid is not so critical. However, if the alkaline metal hydroxide is added in an excess amount and a large amount of substantially free alkaline metal hydroxide is present, the yield is reduced due to decomposition of the glycolonitrile. On the other hand, if the alkaline metal hydroxide is present in a small amount, due to the above-described reason, the reactivity of the aminomethylphosphonic acid is lowered and the yield is also reduced. Accordingly, the alkaline metal hydroxide is preferably added in an amount of from 1.5 to 2.5 equivalents, more preferably from 1.8 to 2.2 equivalents to the aminomethylphosphonic acid.

Alkaline metal hydroxides for use in the present invention include sodium hydroxide, potassium hydroxide, calcium hydroxide and magnesium hydroxide. Sodium hydroxide and potassium hydroxide are preferred.

The amount of glycolonitrile that is used in the reaction, as long as it is within the above-described quantitative range relative to the alkaline metal hydroxide and the aminomethylphosphonic acid, is preferably one equivalent to the theoretical amount of aminomethylphosphonic acid. This value is also not so critical. However, if the amount of glycolonitrile is large relative to the aminomethylphosphonic acid, the excess glycolonitrile causes a side reaction. On the other hand, if the amount of glycolonitrile is small, the aminomethylphosphonic acid which is relatively expensive remains unreacted. Therefore, large deviations from the equivalent amount are not preferred.

Accordingly, the glycolonitrile is preferably used in an amount of from 0.5 to 1.5 equivalents, more preferably from 0.8 to 1.2 equivalents to the aminomethylphosphonic acid.

In this invention, glycolonitrile and aminomethylphosphonic acid dialkali salt react to form N-phosphonomethylglycinonitrile. Instead of the glycolonitrile, a combination of formaldehyde and hydrogen cyanide (or alkali cyanide with the addition of a mineral acid) can be used. This combination is expected to form glycolonitrile, or to serve as glycolonitrile in the reaction with aminomethylphosphonic acid dialkali salt. "Mineral acid" includes, for example, hydrochloric acid or sulfuric acid. "Alkali" means sodium or potassium. The presence of alkali in the reaction is for the formation of an aminomethylphosponic dialkali salt.

The reaction system is not particularly limited. However, to an aqueous solution obtained by mixing and stirring an aminomethylphosphonic acid and an alkaline metal hydroxide, an aqueous glycolonitrile solution is usually added dropwise, and stirring is further continued to complete the reaction.

The reaction temperature of the aminomethylphosphonic acid with glycolonitrile is preferably 60° C. or lower. If the temperature is too high, a side reaction results to thereby reduce the yield.

The time required for the reaction varies depending upon the reaction temperature, but it is approximately from 30 minutes to 3 hours.

According to this reaction, N-phosphonomethylglycinonitrile is obtained as a solution of an alkaline metal salt or a partial alkaline metal salt of N-phosphonomethylglycinonitrile depending upon the amount of the alkaline metal hydroxide that is used. The solution thus obtained can be used as is in the subsequent acidic hydrolysis reaction step. Or, if desired, the solution may be concentrated to isolate an alkaline metal salt of N-phosphonomethylglycinonitrile. Furthermore, the alkaline reaction solution may be neutralized with an acid according to a known method to isolate N-phosphonomethylglycinonitrile, and the product may be purified by a recrystallization method or the like.

2. Hydrolysis of N-phosphonomethylglycinonitrile:

In the present invention, subsequent to the above-described reaction of an aminomethylphosphonic acid with glycolonitrile, or formaldehyde and hydrogen cyanide in situ, under an alkaline condition, the alkaline reaction solution is neutralized and hydrolyzed under an acidic condition. The acid for use in this reaction includes acids that are commonly used in an acidic hydrolysis reaction, such as hydrochloric acid, sulfuric acid, hydrobromic acid, perchloric acid and a strongly acidic ion exchange resin. Among these, hydrochloric acid and sulfuric acid are preferred, and hydrochloric acid is more preferred.

The acid is added in an amount needed to neutralize the reaction solution obtained by reacting an aminomethylphosphonic acid with glycolonitrile under an alkaline condition (namely, an amount needed for neutralizing the alkaline salt of N-phosphonomethylglycinonitrile and the amino group), and further adding the acid in an amount corresponding to at least 0.5 equivalents. The acid is preferably added in an amount needed neutralize the reaction solution plus an amount of from 2 to 6 equivalents of the N-phosphonomethylglycinonitrile. If the amount of the acid is less than the amount needed to neutralize the reaction solution plus 0.5 equivalents, the reaction proceeds at a slow rate, and it is unsuitable for practice in industry. On the other hand, if the amount of the acid is excessive, the resulting N-phosphonomethylglycinone is difficult to isolate and purify, which condition is economically disadvantageous.

The reaction temperature during hydrolysis is set in the vicinity of the reflux temperature. If the temperature is low, the reaction rate is slow and this is not practical.

The reaction time varies depending upon the temperature, however, it is approximately from 3 to 15 hours.

After the hydrolysis reaction, the reaction solution may be concentrated to precipitate and isolate N-phosphonomethylglycine. Alternatively, after adjusting the pH by adding an alkali to the reaction solution and appropriately diluting the reaction solution, N-phosphonomethylglycine may be isolated and purified using other methods known in the art such as purifying with an ion exchange resin, individually or in combination thereof. However, the present invention provides a superior result when the desired N-phosphonomethylglycine is deposited by concentrating the acidic reaction solution. The crude product may further be purified by recrystallization.

According to the present invention, subsequent to a reaction step where N-phosphonomethylglycinonitrile is produced by reacting an aminomethylphosphonic acid with glycolonitrile, or formaldehyde and hydrogen cyanide in situ, under an alkaline condition to convert the same into an N-phosphonomethylglycinonitrile salt or a mixture of an N-phosphonomethylglycinonitrile salt and N-phosphonomethylglycinonitrile, the reaction product is hydrolyzed by adding thereto an acid in a prescribed amount. Accordingly, the use of a large amount of an alkaline metal hydroxide and the neutralization step for obtaining N-phosphonomethylglycine after hydrolysis, which steps are necessary in a conventional alkali hydrolysis method, are omitted in the present invention. Thus, the present invention provides a very useful industrial process for producing N-phosphonomethylglycine.

EXAMPLES

The production process of N-phosphonomethylglycine according to the present invention is described in greater detail below by reference to the following representative Examples. These Examples are set forth to facilitate an understanding of the present invention. However, the present invention should not be construed as being limited thereto.

Example 1

To a 300 ml-volume four-necked flask equipped with a stirrer, a thermometer, a dropping funnel and a reflux condenser were added 50 g of water, 16.7 g (200 mmol) of a 48% aqueous sodium hydroxide solution and 11.1 g (100 mmol) of an aminomethylphosphonic acid and the mixture was stirred. The flask was cooled in an ice water bath, and while keeping the reaction solution at a temperature of 5° C. or lower, 14.3 g (100 mmol) of a 50% glycolonitrile solution was added dropwise over a period of 30 minutes. After completing the dropwise addition, the mixture was stirred at a temperature of 5° C. or lower for 30 minutes. After returning the mixture to room temperature, it was further stirred for 1 hour. Then, 50.7 g (500 mmol) of a 36% aqueous hydrochloric acid solution was added, and the mixture was heat-refluxed for 8 hours with stirring. After completing the reaction, the reaction solution was analyzed by HPLC and was found to contain 89 mmol of N-phosphonomethylglycine. Thus, the reaction yield to N-phosphonomethylglycinonitrile as a raw material was 89%.

The reaction solution was concentrated to about one half of its volume, and was allowed to stand all night to crystallize N-phosphonomethylglycine. The N-phosphonomethylglycine was separated by filtration, washed with water and dried to obtain 11.2 g of a purified product. The purity of this product as determined by HPLC was 96%.

Example 2

The reaction was conducted in the same manner as in Example 1, except for changing the addition amount of the 36% aqueous hydrochloric acid solution from 50.7 g to 71 g (700 mmol) and the heat-refluxing time to 5 hours. After completing the reaction, the solution was analyzed by HPLC and was found to contain 91 mmol of N-phosphonomethylglycine (91% to N-phosphonomethylglycinonitrile as a raw material).

What is claimed is:

1. A method for producing N-phosphonomethylglycine which comprises reacting an aminomethylphosphonic acid with glycolonitrile, or formaldehyde and hydrogen cyanide in situ, under an alkaline condition to obtain a product comprising an N-phosphonomethylglycinonitrile salt or a mixture of an N-phosphonomethylglycinonitrile salt and N-phosphonomethylglycinonitrile, and adding an acid to hydrolyze the product under an acidic condition.

2. The method for producing N-phosphonomethylglycine as claimed in claim 1, which comprises adding the acid for hydrolysis in an amount needed to neutralize the reaction solution obtained by reacting an aminomethylphosphonic acid with glycolonitrile, or formaldehyde and hydrogen cyanide in situ, under an alkaline condition, and further adding the acid in an amount of 0.5 equivalents or more to the N-phosphonomethylglycinonitrile.

3. The method for producing N-phosphonomethylglycine as claimed in claim 1, which comprises reacting an aminomethylphosphonic acid and glycolonitrile, or formaldehyde and hydrogen cyanide in situ, in an amount of from 0.5 to 1.5 equivalents to the aminomethylphosphonic acid in the presence of an alkali metal hydroxide or an alkaline earth metal hydroxide, wherein said alkali metal hydroxide or an alkaline earth metal hydroxide is added in an amount of from 1.5 to 2.5 equivalents to the aminomethylphosphonic acid.

4. The method for producing N-phosphonomethylglycine as claimed in claim 2, which comprises reacting an aminomethylphosphonic acid and glycolonitrile, or formaldehyde and hydrogen cyanide in situ, in an amount of from 0.5 to 1.5 equivalents to the aminomethylphosphonic acid in the presence of an alkali metal hydroxide or an alkaline earth metal hydroxide, wherein said alkali metal hydroxide or an alkaline earth metal hydroxide is added in an amount of from 1.5 to 2.5 equivalents to the aminomethylphosphonic acid.

5. The method for producing N-phosphonomethylglycine as claimed in claim 1, which comprises adding hydrochloric acid or sulfuric acid to hydrolyze the product.

6. The method for producing N-phosphonomethylglycine as claimed in claim 2, which comprises adding hydrochloric acid or sulfuric acid to hydrolyze the product.

7. The method for producing N-phosphonomethylglycine as claimed in claim 3, wherein the alkali metal hydroxide comprises sodium hydroxide or potassium hydroxide.

8. The method for producing N-phosphonomethylglycine as claimed in claim 3, which comprises adding the alkali metal hydroxide or alkaline earth metal hydroxide in an amount of from 1.8 to 2.2 equivalents to the aminomethylphosphonic acid.

9. The method for producing N-phosphonomethylglycine as claimed in claim 2, which comprises further adding the acid in an amount of from 2 to 6 equivalents of the N-phosphonomethylglycinonitrile.

10. The method for producing N-phosphonomethylglycine as claimed in claim 1, wherein hydrogen cyanide is formed in situ by the reaction of an alkali cyanide and a mineral acid.

* * * * *